United States Patent
Labyed (10) Patent No.: US 11,963,824 B2
(45) Date of Patent: *Apr. 23, 2024

(54) SHEAR WAVE IMAGING BASED ON ULTRASOUND WITH INCREASED PULSE REPETITION INTERVAL

(71) Applicant: Siemens Medical Solutions USA, Inc., Malvern, PA (US)

(72) Inventor: Yassin Labyed, Carlsbad, CA (US)

(73) Assignee: Siemens Medical Solutions USA, inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,546

(22) Filed: Aug. 23, 2022

(65) Prior Publication Data

US 2023/0045668 A1 Feb. 9, 2023

Related U.S. Application Data

(62) Division of application No. 15/983,430, filed on May 18, 2018, now Pat. No. 11,452,503.

(51) Int. Cl.
A61B 8/08 (2006.01)

(52) U.S. Cl.
CPC ............ *A61B 8/5207* (2013.01); *A61B 8/485* (2013.01); *A61B 8/5223* (2013.01)

(58) Field of Classification Search
CPC ....... A61B 8/085; A61B 8/485; A61B 8/5207; A61B 8/5223
See application file for complete search history.

(56) References Cited

U.S. PATENT DOCUMENTS

| | | |
|---|---|---|
| 8,758,248 B2 | 6/2014 | Lin et al. |
| 8,961,418 B2 | 2/2015 | Fan |
| 9,554,770 B2 | 1/2017 | Fan et al. |
| 2008/0249408 A1 | 10/2008 | Palmeri et al. |
| 2009/0203997 A1 | 8/2009 | Ustuner |
| 2010/0286516 A1 | 11/2010 | Fan et al. |
| 2012/0089019 A1 | 4/2012 | Fan |
| 2013/0131511 A1 | 5/2013 | Peterson et al. |
| 2013/0245442 A1 | 9/2013 | Hazard et al. |
| 2013/0317361 A1 | 11/2013 | Tabaru et al. |

(Continued)

FOREIGN PATENT DOCUMENTS

| | | |
|---|---|---|
| JP | 2010069295 A | 4/2010 |
| KR | 20120035901 A | 4/2012 |
| KR | 20140000638 A | 1/2014 |

OTHER PUBLICATIONS

Tsuyoshi Shiina, "JSUM Ultrasound Electrography Practice Guidelines Basics and Terminology", 2013 (Year: 2013).*

(Continued)

*Primary Examiner* — Katherine L Fernandez
*Assistant Examiner* — Brooke Lyn Klein (57) ABSTRACT

For shear wave imaging with ultrasound, the apparent pulse repetition frequency is increased by combining displacements from different lateral locations. Different combinations based on different shear wave velocities and corresponding time shifts and/or attenuations and corresponding scalings are tested to find a smooth displacement profile for the combination. Once the smooth displacement profile is found, the corresponding shear wave velocity is estimated or determined.

14 Claims, 3 Drawing Sheets

(56) References Cited

U.S. PATENT DOCUMENTS

| | | |
|---|---|---|
| 2013/0345565 A1 | 12/2013 | Fan et al. |
| 2014/0276058 A1 | 9/2014 | Fan et al. |
| 2015/0087976 A1 | 3/2015 | Fan |
| 2015/0216507 A1 | 8/2015 | Greenleaf et al. |
| 2017/0209117 A1 | 7/2017 | Urban et al. |
| 2019/0076126 A1 | 3/2019 | Greenleaf et al. |

OTHER PUBLICATIONS

Alessandro, Schneebeli, et al. "Shear wave and strain sonoelastography for the evaluation of the Achilles tendon during isometric contractions." Insights into Imaging 12.1 (2021).

Snoj, Žiga, et al. "Ultrasound elastography in musculoskeletal radiology: past, present, and future." Seminars in Musculoskeletal Radiology. vol. 24. No. 02. Thieme Medical Publishers, 2020.

Yeh, Chia-Lun, et al. "Shear wave measurements for evaluation of tendon diseases." IEEE transactions on ultrasonics, ferroelectrics, and frequency control 63.11 (2016): 1906-1921.

* cited by examiner

SHEAR WAVE IMAGING BASED ON ULTRASOUND WITH INCREASED PULSE REPETITION INTERVAL

RELATED CASE

This application is a divisional of U.S. application Ser. No. 15/983,430, filed May 18, 2018, the disclosure of which is incorporated herein by reference.

BACKGROUND

The present embodiments relate to shear wave imaging using ultrasound. In Shear Wave Elasticity Imaging (SWEI), images are formed by tracking the tissue displacements caused by acoustic radiation force impulse (ARFI)-induced shear waves. The maximum pulse repetition frequency (PRF) for tracking the shear wave is determined by the round-trip time of the tracking pulses. In highly stiff media, such as tendons, shear wave travels more rapidly than in soft tissue. The maximum PRF may not be sufficient for tracking the fast shear waves.

Higher PRF may be provided by tracking the shear wave using a sequence of separable signals transmitted in rapid succession. For example, tracking pulses at different frequencies or coded transmit pulses are used to increase the sample rate. This approach may suffer from artifacts caused by clutter noise from the different separable tracking transmissions and from errors caused by displacement estimation using transmit pulses with different frequencies or coding.

SUMMARY

By way of introduction, the preferred embodiments described below include methods, instructions, computer readable media, and systems for shear wave imaging with ultrasound. The apparent PRF is increased by combining displacements from different lateral locations. Different combinations based on different shear wave velocities and corresponding time shifts and/or attenuations and corresponding scalings are tested to find a smooth displacement profile for the combination. Once the smooth displacement profile is found, the corresponding shear wave velocity is estimated or determined.

In a first aspect, a method is provided for shear wave imaging by an ultrasound imaging system. A transducer transmits a pushing pulse. The pushing pulse generates a shear wave in tissue of a patient. The ultrasound imaging system tracks tissue displacements over time at a plurality of locations in a region of interest. The tissue displacements occur in response to the shear wave and are sampled at a first sampling rate for each of the locations. A temporal displacement profile is generated from a combination of the tissue displacements over time of different ones of the locations. The combination uses a time shift and a scaling of at least one of the tissue displacements over time. The temporal displacement profile has a second sampling rate greater than the first sampling rate. A shear wave velocity is estimated using the temporal displacement profile. An image showing of the estimate of the shear wave velocity is displayed.

In a second aspect, a method is provided for shear wave imaging by an ultrasound imaging system. A transducer transmits a pushing pulse, which generates a shear wave in tissue of a patient. The ultrasound imaging system determines displacement profiles of tissue displacements over time at each of a plurality of locations, and the tissue displacements are in response to the shear wave. A combined displacement profile formed from the displacement profiles of the plurality of locations is identified. The combined displacement profile is selected from combinations based on a plurality of tests of different shear wave speeds where the shear wave speed of the different shear wave speeds resulting in a smoothest one of the combinations indicates the combined displacement profile. A shear wave speed is estimated using the identification of the combined displacement profile. An image showing of the estimate of the shear wave velocity is displayed.

In a third aspect, a system is provided for shear wave imaging with ultrasound. An ultrasound scanner is configured to transmit an acoustic radiation force pulse from a transducer into tissue and configured to scan the tissue as the tissue responds to a shear wave generated by the acoustic radiation force pulse. An image processor is configured to generate different profiles, each of the different profiles formed from displacements over time from different locations, to test the different profiles, and to select one of the different profiles. A display is configured to display an image showing a shear wave speed based on the selected profile.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear wave imaging with ultrasound is provided in highly stiff media. Examples of such stiff media in medical imaging include musculoskeletal (MSK) (e.g., tendons), prostate, and hepatic focal lesions. By increasing the apparent PRF, the shear wave velocity may be more accurately estimated even where ultrasound round-trip travel time results in undersampling for a given location. The same approach may be used in less stiff media where tracking frequency is not an issue. This approach increases the effective PRF, resulting in more likely accurate estimation of shear wave velocity.

Displacement profiles from multiple lateral locations are combined. The displacement profiles from the different lateral locations are time-shifted and scaled based on possible shear wave velocity and attenuation. The time-shifted and scaled profiles are combined to form a displacement profile with a higher effective PRF. The shear wave speed is calculated by finding the time shift that yields the smoothest or sufficiently smooth displacement profile.

Figure 1:
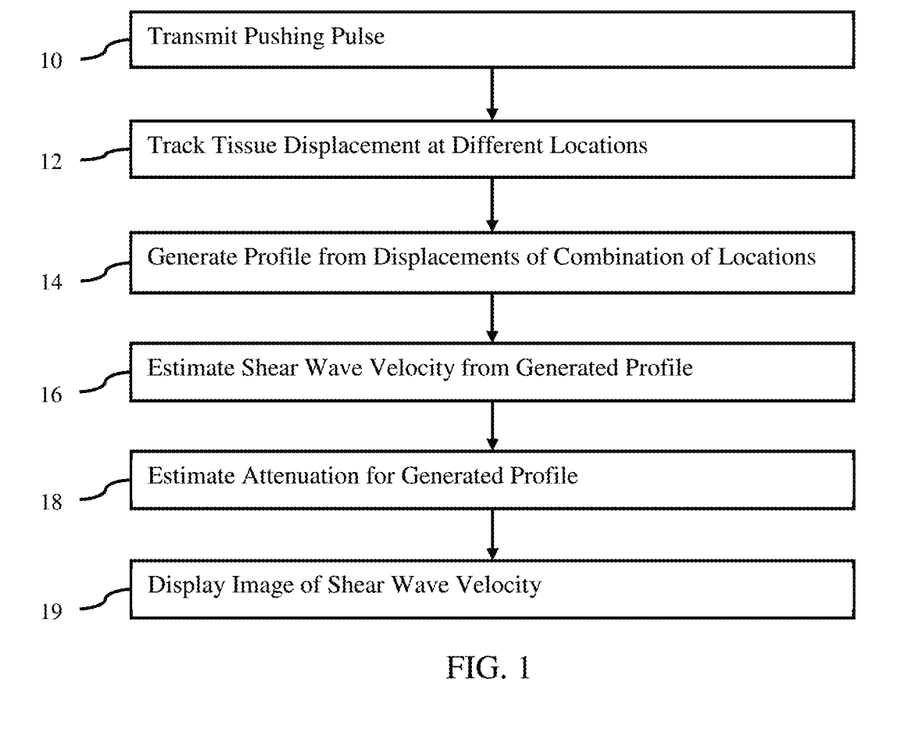
FIG. 1 is a flow chart diagram of one embodiment of a method for shear wave imaging by an ultrasound imaging system.

FIG. 1 shows one embodiment of a method for shear wave imaging by an ultrasound imaging system. For shear waves traveling at higher speeds, the sampling frequency provided by ultrasound for tracking may be relatively infrequent, resulting in under sampling and less accurate estimation of shear wave velocity. To increase the effective sampling rate, the displacements over time from different locations are combined. The combination having a displacement profile closest to a norm provides displacements at a greater sampling frequency for more accurate estimation of shear wave velocity.

Figure 5:
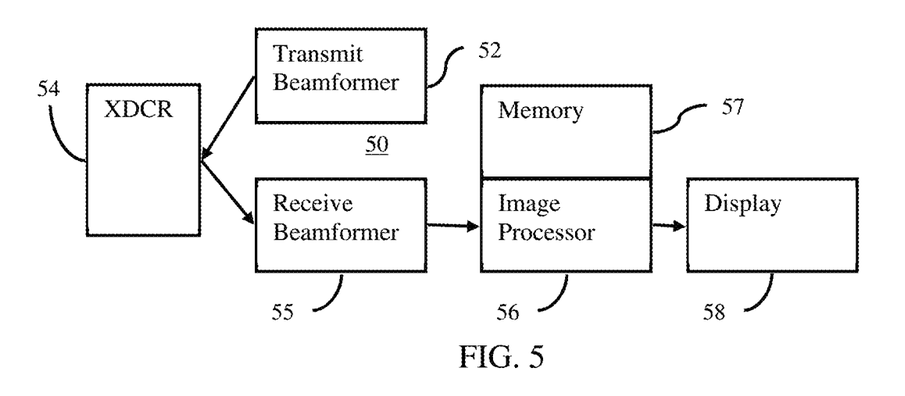
FIG. 5 is a block diagram of one embodiment of a system for shear wave imaging with ultrasound.

The acts are performed with an ultrasound imaging system, such as the system described for FIG. 5. A transducer and/or beamformers are used to acquire data, and an image processor estimates displacements from the data and shear wave speed and/or attenuation from the displacements. The ultrasound imaging system outputs the shear wave speed. Other devices, such as a computer or detector, may be used to perform any of the acts.

Additional, different, or fewer acts may be provided in the method of FIG. 1. For example, act 18 is not provided. As another example, act 16 is not provided. In yet another example, acts for configuring the ultrasound system to scan the patient are provided.

The acts are performed in the order described or shown (e.g., top to bottom or numerical). Other orders may be provided, such as by repeating the acts for another region of interest. In one example, acts 16 and 18 are performed as part of act 14 or in a reverse order.

In acts 10 and 12, the ultrasound system generates and detects a shear wave at different locations in tissue of a patient. An acoustic radiation impulse excitation (ARFI or pushing pulse) or other source of stress generates a shear wave in tissue. As the shear wave propagates through the tissue, the tissue displaces. The shear wave is detected from displacements of tissue caused by the shear wave passing. By scanning the tissue with ultrasound, the data for calculating the displacements over time is acquired. Using correlation or other similarity measure, the displacements represented by the scans acquired at different times are determined. The ultrasound system acquires tissue displacements over time (i.e., displacement profiles) for different locations.

In act 10, a beamformer generates electrical signals for focused ultrasound transmission, and a transducer converts the electrical signals to acoustic signals for transmitting the pushing pulse from the transducer to a focal region. ARFI is used. An acoustic excitation is transmitted into a patient. The acoustic excitation acts as an impulse excitation for causing a shear wave. For example, a 400 cycle transmit waveform with power or peak amplitude levels similar or lower than B-mode transmissions for imaging tissue is transmitted as an acoustic beam. In one embodiment, the transmission is a shear wave generating sequence applied to the field of view. Any ARFI or shear wave imaging sequence may be used. Other sources of stress may be used, such as a thumper (mechanical impact or vibration source).

The transmission is configured by power, amplitude, timing, or other characteristic to cause stress on tissue sufficient to displace the tissue at a focal location. For example, a transmit focus of the beam is set relative to a field of view or region of interest (ROI) to cause the generated shear wave displacement throughout the field of view or ROI. The impulse excitation generates a shear wave at a spatial location. Where the excitation is sufficiently strong, the shear wave is generated. The shear wave propagates transversely through tissue more slowly than the longitudinal wave propagates along the acoustic wave emission direction, so the type of wave may be distinguished by timing and/or direction. The displacement of the tissue due to the shear wave is greater at locations closer to the focal location at which the wave is generated. As the wave travels, the magnitude of the wave attenuates. The stiffness of the tissue affects the shear wave speed and/or attenuation.

In act 12, tissue displacements are tracked. The ultrasound system, such as an image processor of the system, tracks the displacements caused in response to the pushing pulse. For each of a plurality of locations, the displacement caused by the propagating shear wave is tracked. The tracking is axial (i.e., tracking displacements one-dimensionally along a scan line), but may be two or three-dimensional tracking. The locations that are tracked are distributed laterally (e.g., perpendicular to the scan line), but may be distributed in two or three dimensions.

The tracking is over time. The tissue displacements for each location are found for any number of temporal samplings over a period during which the wave is expected to propagate by the location. Due to poor PRF for rapidly traveling shear waves, the temporal sampling may be under sampled. By tracking at multiple locations, tissue displacement profiles of displacement over time for the different locations are provided.

The period for tracking may include times prior to the transmission of the pushing pulse and/or shear wave reaching each given location. Similarly, the period for tracking may include times after the tissue relaxes or the entire shear wave has propagated past each location. While the shear wave propagates past the locations, the tissue is scanned.

A transducer and beamformer acquire echo data at different times to determine the displacement of the tissue. The displacement is detected with ultrasound scanning. At least some of the ultrasound data is responsive to displacement caused by the shear wave or pressure. A region, such as a region of interest, entire field of view, or sub-region of interest, is scanned with ultrasound. The region is monitored to detect the wave. The echo data represents the tissue when subjected to different amounts of pressure at different times. The region is any size, such as 5×5 mm in lateral and 10 mm in axial. For example, B-mode scans are performed to detect tissue displacement. Any sampling or beamformer resolution may be used, such as measuring on a linear grid with sample locations every 0.25 mm. Doppler, color flow, or other ultrasound mode may be used to detect displacement.

For a given time, ultrasound is transmitted to the tissue or region of interest. Any now known or later developed displacement imaging may be used. For example, pulses with 1-5 cycle durations are used with an intensity of less than 720 mW/cm$^2$ (e.g., B-mode pulses). Pulses with other intensities may be used. The scanning is performed for any number of scan lines. For example, eight or sixteen receive beams distributed in two-dimensions are formed in response to each transmission. After or while applying stress, B-mode transmissions are performed repetitively along a single transmit scan line and receptions along adjacent receive scan lines. In other embodiments, other numbers of receive beams are formed in response to each transmission. Additional transmit scan lines and corresponding receive line or lines may be used. Any number of repetitions may be used, such as about 120 times or over 15 ms or less for more rapid shear waves.

The B-mode intensity may vary due to displacement of the tissue over time. An ongoing or sequence of displacements is detected for each of the locations. For the monitored scan lines, a sequence of data is provided representing a time profile of tissue motion resulting from the stress. By performing the transmitting and receiving multiple times, data representing the region at different times is received.

The displacement is detected for each of multiple spatial locations. Any number of sample positions may be measured for displacement, such as measuring every quarter millimeter in the 10×5 mm region of interest. The displacement profile is determined at each sample point or data from two or more sample points are combined to give a displacement profile for a sub region. Displacement for each sample point and for each sample time is measured.

The velocity, variance, shift in intensity pattern (e.g., speckle tracking), or other information is detected from the received data as the displacement between two times. In one embodiment using B-mode data, the data from different scans is axially correlated as a function of time. For each depth or spatial sampling position, a correlation over a plurality of depths or spatial sampling positions (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations between the two data sets are performed.

The reference is a first or other set of data or data from another scan. The reference set is from before the stress but may be from after the stress. The same reference is used for the entire displacement detection, or the reference data changes in an ongoing or moving window.

The level of similarity or correlation of the data at each of different offset positions is calculated. The translation with a greatest correlation represents the displacement or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

Figure 2:
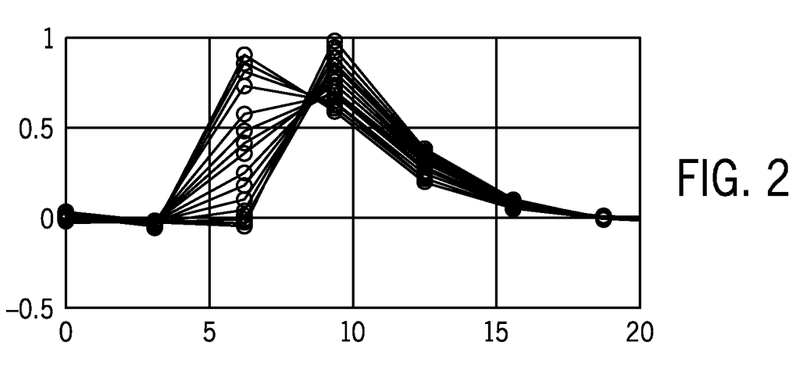
FIG. 2 illustrates sparse sampling of displacements at different locations for a shear wave in stiff media.

The displacement of the tissue starts from a steady state from prior to the shear wave arriving, then the displacement increases to a maximum, after which the displacement decays back to the steady state. Other displacement profiles are possible. FIG. 2 shows example displacement profiles of displacements over time for sixteen adjacent locations. Due to under sampling, the typically gradual curve is not provided. In this example, there are seven times at which the tissue is scanned for tracking. For each lateral location, the peak in the displacement from the shear wave should occur in time between the peaks of the adjacent locations. With under sampling, the shear wave appears to occur at one group of locations at one time (about 6 µs) and appears to occur at another group of locations at another time (about 9 µs). Greater or lesser amounts of under sampling by the sampling rate of the ultrasound tracking for each location may be provided. The accuracy of estimating shear wave from the under sampled displacement profiles is poor.

In act 14, the image processor generates a temporal displacement profile from a combination of the tissue displacements over time of different ones of the locations. To increase the effective PRF, displacements from different locations are used to create a displacement profile with a greater sampling rate. Since the peak of the shear wave at any given sample time is at one location and not others, the combination provides a profile with a greater sampling rate.

The combination is of displacements or displacement profiles from two or more locations. Since the displacement profiles themselves are not being correlated to detect shift and corresponding shear velocity, displacements from three or more locations may be combined. For example, displacements from four, eight, sixteen or thirty-two laterally spaced locations are combined. One combination is provided for the region of interest to estimate a shear wave velocity for that region.

In another embodiment, a window defining location is used. The window is centered at one location for one combination. The window is spatially shifted to be centered elsewhere for another combination. The tracking sample locations in the window for each setting of window position are combined. As a result, different combinations are provided for different groups of locations, allowing for spatial estimation of velocity (i.e., different shear wave velocities for different locations—center of the window at different positions).

Different possible combinations are tested. A plurality of test combinations are formed. The possible combinations iterate over shear wave speed and/or attenuation. Given a shear wave speed, time shifts are computed for individual displacement profiles. The final shear wave speed is one that yields the smoothest combined profile. Similarly, the possible combinations iterate over shear wave attenuation coefficient. Given an attenuation coefficient, scaling factors are computed for individual displacement profiles. The final attenuation coefficient is one that yields the smoothest combined profile. One of the possible combinations is selected to provide the velocity and/or attenuation based on the time shift and/or scaling resulting in a sufficiently smooth combination displacement profile.

Each combination is formed with a time shift and/or scale. Different time shifts and scales corresponding to different velocities and attenuations are tested. One displacement profile is used as a reference, and the others displacement profiles in the combination are temporally shifted and/or scaled based on a time shift and/or scale provided by the velocity and/or attenuation being tested. Different combinations corresponding to different shifts and scales are tested.

For example, each combination is formed with a time shift and/or scale. The time shifts and scales of the different individual profiles are different based on the different locations. Using four displacement profiles to form the combination, the first one is the reference. The other three profiles are time-shifted and scaled. The amount by which each of the three profiles is shifted and scaled is different. Given 1 mm between any two adjacent ones of the four lateral locations, time shifts are applied based on the velocity being tested. In the first iteration, the check is whether the shear wave speed is 4 m/s=4 mm/ms. Profile 1 is not shifted; profile 2 is shifted by $t=d/vs=1$ mm/4 mm/ms=0.25 ms; profile 3 is shifted by $t=d/vs=2$ mm/4 mm/ms=0.5 ms; and profile 4 is shifted by $t=d/vs=3$ mm/4 mm/ms=0.75 ms. The resulting combined displacement profile obtained by combining all four profiles is the one tested for smoothness.

When there are just two locations, a single time shift and/or single scale are provided for each velocity and/or attenuation.

Any search pattern may be used where a sequence of time shifts and scales are tested based on the velocities and attenuations. Different iterations are tested. In one embodiment, different velocities and corresponding time shifts are tested. Once a velocity is selected, different attenuations and corresponding scales are tested. Attenuation may be tested, and then velocity. In another embodiment, only attenuation or only velocity is tested. In yet another embodiment, both attenuation and velocity are altered for each iteration. In another embodiment, a looping iteration is used. Different velocities are tested, then different attenuations are tested using the selected velocity, then different velocities are tested using the selected attenuation and centered on the previously selected velocity. Any number of loops through this process may be used.

The initial time shifts and/or scales applied may be based on an expected shifts and/or scales (i.e., expected velocity and/or attenuation). The type of tissue being imaged or for which shear wave speed is being measured may be indicated by user input. The initial shifts and/or scales are based on the indication of tissue. Other shifts and/or scales offset from the initial ones are tested as well.

The scale may be a given value or may be a linear scale over location. Locations further from the reference are scaled by an amount given by the attenuation and the distance from the reference location. For time shift, the time shift is cumulative. The further location from the reference location, the greater the time shift. The amount of time shifts as a function of distance is varied with the velocity.

Figure 3:
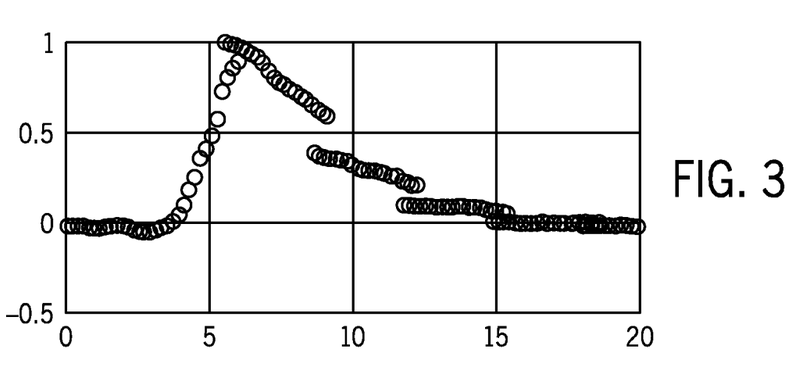
FIGS. 3 and 4 illustrate example combined displacement profiles from the displacements of different locations of FIG. 2, where the combined displacement profile of FIG. 4 is smoother than the combined displacement profile of FIG. 3.
Figure 4:
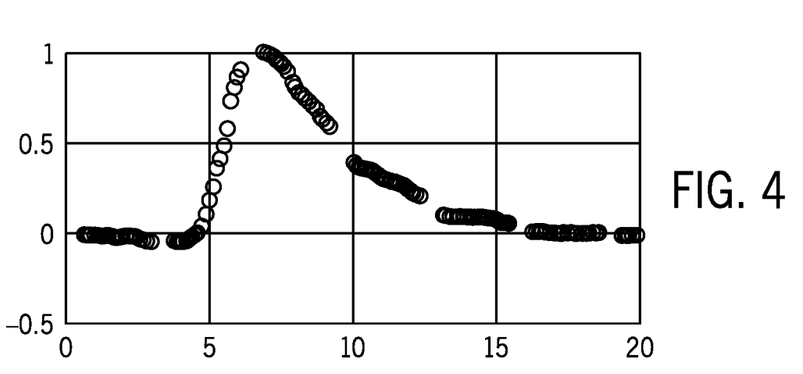

After applying the time shifts and/or scales for a given velocity and/or attenuation, the resulting displacements from the different locations are combined into a single displacement profile. FIGS. 3 and 4 show two such combinations from the displacements of FIG. 2. FIG. 3 represents one possible combination from one velocity and corresponding time shifts applied across the locations based on location spacing. FIG. 4 represents another possible combination from another velocity and corresponding time shifts.

The combination providing the smoothest or sufficiently smooth displacement profile is selected. The displacements caused by a propagating shear wave have a normal (i.e., typical) or expected shape of the distribution over time. Each possible combination is tested to determine a level of smoothness or match to the norm. The combination with the smoothest or most normal distribution is selected or identified. In other embodiments, a threshold level of smoothness or normalness is applied. Once a combination with sufficient smoothness or normalness is found, the search ends.

The level of smoothness may be measured in any manner. FIG. 4 shows a combination with greater smoothness than FIG. 3. The size of the temporal and/or amplitude gaps may be measured where smaller size gaps indicates greater smoothness. In another approach, the combination of displacements from the different locations is transformed into the frequency domain. A Fourier transform is applied to the displacement profile formed by the combination. The amount of high frequency content is quantified. Lower high frequency content indicates a smoother profile. In yet another approach, the combined displacement profile is matched to a template. The template or default represents the norm. The level of similarity (e.g., correlation coefficient) of the combined displacement profile to the template indicates the level of smoothness. Other measures of smoothness or normalness may be used.

The combination formed by a time shift and/or scale resulting in the smoothest (or most normal) or sufficiently smooth (or normal) displacement profile is selected. The different possible combinations are tested. In the examples of FIGS. 3 and 4, the displacement profile from the combination resulting in FIG. 4 is selected. The selection identifies a time shift and/or scale that results in the combination.

Due to the combination of displacements from different locations into one profile, the effective sampling rate is increased. For example, the effective sampling rate for the displacement profile of FIG. 4 is 16 times the sampling rate of any of the displacement profiles for a single location of FIG. 2. As a result, a more complete or better sampled displacement profile is provided, allowing for estimation of shear wave velocity from a greater amount of information (i.e., more samples).

In act 16, the image processor estimates a shear wave velocity using the temporal displacement profile. The shear wave speed in the tissue of the patient is determined. The selected or identified combined displacement profile is used. This relatively or sufficiently smooth or normal combination displacement profile with the corresponding greater PRF relative to the PRF of the displacements over time for a location identifies the shear wave velocity.

In one embodiment, the shifts that resulted in the combination indicates the shear wave velocity. The time shifts for the selected combination are based on a shear wave velocity. The selection of the combination indicates the locations-based time shifts resulting from a given velocity, which provides the estimate of velocity. In alternative embodiments, different combinations are selected for different spatial windows or sub-regions. The resulting combinations may be correlated with each other to provide a phase shift between the combinations. The distance between the centers of the window for the different combinations and the phase shift from the greatest correlation indicate the shear wave velocity.

In act 18, the image processor estimates an attenuation. The attenuation is estimated using the selected combination displacement profile. The scales for the selected combination indicates a rate of change in amplitude over distance. The scaling applied to the displacements maps to the attenuation of the shear wave. Attenuation is an exponential function: $\exp^{(\alpha * d)}$ where $\alpha$ is the attenuation coefficient and d is the lateral location or distance from a reference location. The scalings resulting in the smooth or normal displacement profile indicates the shear wave attenuation in the tissue. Attenuation as a function of location (i.e., spatial window placement) may be determined.

In act 19, the image processor transmits the estimate of the shear wave velocity, estimate of the shear wave attenuation, and/or both. The transmission is to a display, memory, or network. For example, the transmission is an output from or within the ultrasound imaging system.

In one embodiment, an image showing the estimate of the velocity and/or attenuation is output. The value for the region of interest is provided on a B-mode image or other ultrasound image. The value and/or values for the velocity and/or attenuation are output as text, a number, or coded in a graph. For example, the user selects a location on a B-mode image. In response, the ultrasound system calculates the value for the shear wave velocity for a region centered at the selected location. A numerical, textual, and/or graphical representation of the calculated value is overlaid on the B-mode image, displayed independently, or otherwise communicated to the user (e.g., added to a report).

Where velocities are estimated for different locations, an image of shear velocity spatial distribution is generated. For example, a shear wave velocity image is color modulated based on shear velocity as a function of location in the region of interest. The shear wave velocity image is overlaid on a B-mode image covering a larger field of view than the region of interest or shear wave velocity image. Alternatively, the brightness, tent, hue, or color map is based on the velocity. In other embodiments, other types of elasticity imaging, no shear or elasticity image, and/or different types of ultrasound imaging are provided.

FIG. 5 shows one embodiment of a system 50 for shear wave imaging with ultrasound. The system 50 implements the method of FIG. 1 or other methods. Displacements as a function of time from different locations are combined into a displacement profile with a greater effective PRF for estimating a shear wave characteristic in the tissue of a patient.

The system 50 includes a transmit beamformer 52, a transducer 54, a receive beamformer 55, an image processor 56, a display 58, and a memory 57. Additional, different or fewer components may be provided. For example, a user input is provided for user interaction with the system, such as to select a location for which a measurement is to occur or to designate placement of a region of interest.

The system 50 is a medical diagnostic ultrasound imaging system or ultrasound scanner. The system 50 is configured to transmit an acoustic radiation force impulse from the transducer 54 into tissue and to scan the tissue at a plurality of locations as the tissue responds to a shear wave created by the acoustic radiation force impulse. The response to the shear wave is tracked by the ultrasound scanner. In alternative embodiments, the system 50 includes a front-end scanner and a back-end processor, such as a personal computer, workstation, PACS station, or other arrangement at a same location or distributed over a network for real-time or post acquisition imaging. The scanning components (e.g., transmit beamformer 52, transducer 54, and receive beamformer 55) are part of a different device than the memory 57, image processor 56, and/or display 58. The back-end may acquire data from a memory or from transfer over a network. The front-end provides the data to the memory or network.

The transmit beamformer 52 is an ultrasound transmitter, memory, pulser, analog circuit, digital circuit, or combinations thereof. The transmit beamformer 52 is configured to generate waveforms for a plurality of channels with different or relative amplitudes, delays, and/or phasing. Upon transmission of acoustic waves from the transducer 54 in response to the generated electrical waveforms, one or more acoustic beams are formed. A sequence of transmit beams are generated to scan a region. Sector, Vector®, linear, or other scan formats may be used. In alternative embodiments, the transmit beamformer 52 generates a plane wave or diverging wave for more rapid scanning. The same region is scanned multiple times. For shear imaging, a sequence of scans along the same lines is used.

The same transmit beamformer 52 may generate impulse excitations (ARFI or pushing pulse) and acoustic beams for tracking. Electrical waveforms for ARFI are generated, and then electrical waveforms for tracking are generated. In alternative embodiments, a different transmit beamformer is provided for generating the ARFI than for tracking. The transmit beamformer 52 causes the transducer 54 to generate acoustic energy. Using delay profiles across channels, the transmit beamformer 52 steers the pushing pulse to the desired focal position or positions and scans for tracking displacements.

The transducer 54 is an array for generating acoustic energy from electrical waveforms. For an array, relative delays focus the acoustic energy. A given transmit event corresponds to transmission of acoustic energy by different elements at a substantially same time given the focusing delays. The transmit event may provide a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time due to shear wave propagation. A tracking pulse may be B-mode transmission, such as using 1-5 cycles waveforms. The tracking pulses are used to scan a region of a patient undergoing a change in stress.

The transducer 54 is a 1-, 1.25-, 1.5-, 1.75- or 2-dimensional array of piezoelectric or capacitive membrane elements. A wobbler array may be used. The transducer 54 includes a plurality of elements for transducing between acoustic and electrical energies. Receive signals are generated in response to ultrasound energy (echoes) impinging on the elements of the transducer 54. The elements connect with channels of the transmit and receive beamformers 52, 55.

The receive beamformer 55 includes a plurality of channels with amplifiers, delays, and/or phase rotators, and one or more summers. Each channel connects with one or more transducer elements. The receive beamformer 55 is configured by hardware or software to apply relative delays, phases, and/or apodization to form one or more receive beams in response to each imaging or tracking transmission. The receive operation may not occur for echoes from the impulse excitation used to displace tissue. The receive beamformer 55 outputs data representing spatial locations using the receive signals. Relative delays and/or phasing and summation of signals from different elements provide beam formation. In alternative embodiments, the receive beamformer 55 is a processor for generating samples using Fourier or other transforms.

In coordination with the transmit beamformer 52, the receive beamformer 55 generates data representing a region at different times. After the ARFI, the receive beamformer 55 generates beams representing locations along one or a plurality of lines at different times. By scanning the region with ultrasound, data (e.g., beamformed samples) is generated. By repeating the scanning, ultrasound data representing the region at different times after the impulse excitation is acquired.

The receive beamformer 55 outputs beam summed data representing different sample positions. Dynamic focusing may be provided. The data may be for different purposes. For example, different scans are performed for B-mode or tissue data than for shear ultrasound imaging. Alternatively, the B-mode data is also used to track the shear wave. As another example, data for shear imaging is acquired with a series of shared scans, and B-mode or Doppler scanning is performed separately or using some of the same data. The ultrasound or echo data is from any stage of processing, such as beamformed data before detection or data after detection.

The memory 57 is a non-transitory computer readable storage media. For example, the memory 57 is a cache, buffer, RAM, removable media, hard drive or other non-transitory computer readable storage media. Computer readable storage media include various types of volatile and nonvolatile storage media.

The memory 57 is configured by the image processor 56, a controller, or a memory processor to store and provide data. The memory 57 stores any of the data used to estimate the shear wave characteristics. For example, the ultrasound data (beamformed data and/or detected data), displacements, displacement profile, time shifts, scalings, level of smoothness, velocities, and/or attenuations are stored.

The image processor 56 operates pursuant to instructions stored in the memory 57 or another memory for estimating the shear wave velocity and/or attenuation of tissue of a patient. The instructions for implementing the processes, methods and/or techniques discussed herein are provided on the computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The image processor 56 includes a B-mode detector, Doppler detector, pulsed wave Doppler detector, correlation processor, and/or Fourier transform processor for detecting and processing information for display from beamformed ultrasound samples.

In one embodiment, the image processor 56 includes one or more detectors and a separate processor. The separate processor is a control processor, general processor, digital signal processor, application specific integrated circuit, field programmable gate array, network, server, group of processors, graphics processing unit, digital signal processor, analog circuit, digital circuit, combinations thereof, or other now known or later developed device for estimating a characteristic of a shear wave in tissue. For example, the separate processor is configured by hardware, firmware, and/or software to perform any combination of one or more of the acts 12-19 shown in FIG. 1.

The image processor 56 is configured to measure displacement profiles (i.e., displacements as a function of time) for a plurality of locations. For example, the beamformed data or detected data are axially correlated with a reference to determine an amount of displacement of the tissue for a given time at each of a plurality of scan lines. The locations are sample positions of the receive beamformer 55 or sub regions of a region of interest. A displacement profile of displacement over time for each of different locations is generated. For example, 16 displacement profiles for a respective 16 laterally spaced locations are generating.

The image processor 56 is configured to generate different displacement profiles from different combinations of the profiles from different locations. Different time shifts and/or scalings are applied to form different combinations based on different speeds and/or attenuation. The resulting combinations of displacements (i.e., combination profiles) from different locations are tested. The test determines a level of similarity to a norm or smoothness. Based on the test, one of the combination profiles is selected. For example, the combination of displacements from different locations based on time shifts for a given speed and/or scales for a given attenuation is selected as having a greatest or sufficient level of smoothness.

The image processor 56 is configured to estimate the shear wave speed. By iteration over shear wave speeds and the resulting time shifts, the speed for the selected one of the different profiles is the speed of the shear wave in the patient. The distance between the sample locations is considered as part of the application of the time shift. The combinations resulting from various speeds and corresponding time shifts are tested, so the combination selected based on the test indicates the speed for the shear wave in the tissue. As a result, the testing of the combinations provides the shear wave velocity. Similarly, the scaling provides the attenuation.

The image processor 56 is configured to generate one or more images. The image includes a color modulated region and/or alphanumeric text representing or based on the value of the velocity or attenuation, such as an annotation on an image of a 2D or 3D representation of the tissue. The value of the velocity and/or attenuation is displayed as text, numerically, and/or in a graph separate from or an annotation on any spatial representation of the tissue. Where a spatial distribution of velocity and/or attenuation is estimated, an image of velocity or attenuation spatial distribution may be generated. The image is presented as an overlay or region of interest within a B-mode image or separately.

The display 58 is a CRT, LCD, projector, plasma, or other display for displaying a value, graph, two-dimensional images, or three-dimensional representations. The two-dimensional images represent spatial distribution in an area, such as a plane. The three-dimensional representations are rendered from the data representing spatial distribution in a volume. The display 58 is configured by the image processor 56 or other device by input of the signals to be displayed as an image. The display 58 displays an image representing the estimated value. For example, the image shows the shear wave speed based on the selected combination displacement profile.

Due to the combination profile, the shear wave speed providing on the image is more accurate and/or is provided for stiff media that would otherwise be under sampled. As a result, the physician is provided with more accurate information to diagnosis, prognosis, and/or treatment. For example, the physician may be better able to determine whether a lesion should be biopsied. This may avoid unneeded surgical procedures.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for shear wave imaging with ultrasound, the system comprising:
an ultrasound scanner configured to transmit, from a transducer with an array of elements, a pushing pulse, the pushing pulse operable to generate a shear wave in tissue of a patient, the ultrasound scanner configured to track tissue displacements over time at a plurality of locations in a region of interest, the tissue displacements being in response to the shear wave, the tissue displacements over time being at a first sampling rate provided for each of the locations;
an image processor configured to determine an initial shear wave velocity from a type of tissue and other possible shear wave velocities as offsets from the initial shear wave velocity, configured to iteratively test different temporal displacement profiles formed as different combinations of the tissue displacements over time from the locations, wherein the different combinations are formed from applying different time shifts to the tissue displacements over time for the locations based on the initial and the possible shear wave velocities, each of the different combinations formed from the tissue displacements of multiple locations of the plurality of the locations and a different one of the initial and possible shear wave velocities than others of the different combinations where the different ones of the initial and possible shear wave velocities for the different combinations relates to the different time shifts based on distance, configured to select a first temporal displacement profile of the different temporal displacement profiles, the first temporal displacement profile having a second sampling rate greater than the first sampling rate, and configured to estimate a tissue shear wave velocity from the time shift for the selected first temporal displacement profile as the initial or possible shear wave velocity used to form the selected first temporal displacement profile;

a display configured to display an image showing of the estimate of the tissue shear wave velocity.

2. The system of claim 1 wherein the ultrasound scanner is configured to transmit the pushing pulse as an acoustic radiation force impulse.

3. The system of claim 1 wherein the image processor is configured to select the combination for the first temporal displacement profile as having a greater smoothness level than others of the combinations.

4. The system of claim 1 wherein the image processor being configured to select comprises being configured to select as an identification of the combination matching a norm.

5. The system of claim 1 wherein the image processor is configured to test by generation of the combinations as combinations of three or more of the tissue displacements over time of three or more of the locations.

6. The system of claim 1 wherein the image processor is configured to determine the initial shear wave velocity from the type of tissue where the type of tissue is indicated in an input.

7. The system of claim 1 wherein the image processor is configured to form the different combinations based on the distances of the locations from a focus of the pushing pulse.

8. The system of claim 1 wherein the image processor is configured to form the different combinations where one of the tissue displacements over time is not time shifted.

9. The system of claim 2 wherein the ultrasound scanner is configured to transmit the pushing pulse to a focal position and to track with the locations spaced laterally from the focal location.

10. The system of claim 3 wherein the image processor is configured to select using high frequency content in a frequency domain as a measure of the smoothness level of the tissue displacements.

11. The system of claim 3 wherein the image processor being configured to select comprises being configured to select as a measure of a match to a template.

12. The system of claim 6 wherein the input comprises a user input.

13. The system of claim 1 wherein the image processor is configured to form the different combinations from applying the different time shifts and applying different scalings.

14. The system of claim 7 wherein the image processor is configured to form the different combinations as the different time shifts in the tissue displacements over time for the locations where an amount of the different time shift of each of the different combinations of the tissue displacements for each location is the distance divided by the initial or possible shear wave velocity.

* * * * *